(12) United States Patent
Yamanaka et al.

(10) Patent No.: US 12,064,597 B2
(45) Date of Patent: Aug. 20, 2024

(54) FLUID CONTROL DEVICE

(71) Applicant: Murata Manufacturing Co., Ltd., Kyoto (JP)

(72) Inventors: Yoshio Yamanaka, Kyoto (JP); Yoshihide Amagai, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 987 days.

(21) Appl. No.: 17/028,194

(22) Filed: Sep. 22, 2020

(65) Prior Publication Data

US 2021/0001041 A1 Jan. 7, 2021

Related U.S. Application Data

(63) Continuation of application No. PCT/JP2019/017941, filed on Apr. 26, 2019.

(30) Foreign Application Priority Data

May 9, 2018 (JP) .................. 2018-090535

(51) Int. Cl.
*A61M 5/168* (2006.01)
*A61M 5/172* (2006.01)
*H04N 23/00* (2023.01)

(52) U.S. Cl.
CPC .......... *A61M 5/1689* (2013.01); *A61M 5/172* (2013.01); *H04N 23/00* (2023.01); *A61M 2205/3306* (2013.01)

(58) Field of Classification Search
CPC .............. A61M 5/1689; A61M 5/1411; A61M 2205/3306
See application file for complete search history.

(56) References Cited

U.S. PATENT DOCUMENTS

| 4,038,982 A | 8/1977 | Burke et al. |
| 4,668,216 A | 5/1987 | Martin et al. |
| (Continued) | | |

FOREIGN PATENT DOCUMENTS

| JP | S5268778 A | 6/1977 |
| JP | S63503368 A | 12/1988 |
| (Continued) | | |

OTHER PUBLICATIONS

International Search Report issued in Application No. PCT/JP2019/017941, dated Aug. 6, 2019.

(Continued)

*Primary Examiner* — Courtney B Fredrickson
(74) *Attorney, Agent, or Firm* — Pearne & Gordon LLP

(57) ABSTRACT

A fluid control device 1 includes a casing 10 configured to house a cylindrical infusion tube 100 and a droplet detecting section 60 configured to detect the amount of droplets dripping from a nozzle 124 in the infusion tube 100 housed in the casing 10. The infusion tube 100 includes a flange protruding outward. The casing 10 includes an engagement member 30. The engagement member 30 includes a flange configured to engage with the flange in the infusion tube 100 in a direction along the longitudinal direction of the infusion tube 100 and fix the infusion tube and a fixation surface configured to fix the infusion tube 100 in a direction orthogonal to the longitudinal direction of the infusion tube 100.

8 Claims, 7 Drawing Sheets

(56) References Cited

U.S. PATENT DOCUMENTS

| | | | |
|---|---|---|---|
| 4,673,397 A | | 6/1987 | Lynn et al. |
| 4,986,821 A | * | 1/1991 | Kamen ............... A61M 5/1689 |
| | | | 604/251 |
| 5,147,313 A | | 9/1992 | Dikeman |
| 6,491,659 B1 | * | 12/2002 | Miyamoto .......... A61M 5/1689 |
| | | | 604/30 |
| 2017/0216521 A1 | * | 8/2017 | Kolko ....................... G01F 3/00 |
| 2017/0304535 A1 | * | 10/2017 | Hirata ............... A61M 5/16877 |
| 2018/0177942 A1 | * | 6/2018 | Hirata ............... A61M 5/16804 |

FOREIGN PATENT DOCUMENTS

| | | |
|---|---|---|
| JP | H03297473 A | 12/1991 |
| JP | H04120751 U | 10/1992 |
| JP | 2017086907 A | 5/2017 |
| WO | 2017033947 A1 | 3/2017 |

OTHER PUBLICATIONS

Written Opinion issued in Application No. issued in Application No. PCT/JP2019/017941, dated Aug. 6, 2019.

\* cited by examiner

FLUID CONTROL DEVICE

This is a continuation of International Application No. PCT/JP2019/017941 filed on Apr. 26, 2019 which claims priority from Japanese Patent Application No. 2018-090535 filed on May 9, 2018. The contents of these applications are incorporated herein by reference in their entireties.

BACKGROUND OF THE DISCLOSURE

Field of the Disclosure

The present disclosure relates to fluid control devices.

Description of the Related Art

When transfusion or the like is administered to patients by infusion, a device for adjusting the amount of drips (quantity of flow) of the infusion by adjusting the degree of opening of an infusion channel is used (see, for example, Patent Document 1). In such a device, an infusion tube is inserted from the front of the device, the number of droplets dropping from a lower end of a nozzle inside the infusion tube is counted, and the amount of drips is controlled in accordance with the counted number.

Patent Document 1: Japanese Unexamined Patent Application Publication No. 2017-86907

BRIEF SUMMARY OF THE DISCLOSURE

If the infusion tube in the above-described device for adjusting the amount of drips of the infusion is misaligned or inclined, the accuracy of detecting the droplets may be decreased or the control on the amount of drips may be affected. Thus, it is necessary to position the infusion tube more accurately.

It is an object of the present disclosure to provide a fluid control device capable of performing accurate positioning.

A fluid control device being an embodiment of the present disclosure includes a casing configured to house a tubular infusion tube including a nozzle from which fluid drips and a droplet detecting section configured to detect an amount of droplets dripping from the nozzle in the infusion tube housed in the casing. The infusion tube includes a flange protruding outward. The casing includes a first fixation section configured to engage with the flange in a direction along a longitudinal direction of the infusion tube and fix the infusion tube and a second fixation section configured to fix the infusion tube in a direction orthogonal to the longitudinal direction of the infusion tube.

With that configuration, the position of the infusion tube in the longitudinal direction of the infusion tube is fixed by the first fixation section, its position in the direction orthogonal to the longitudinal direction is fixed by the second fixation section, and it can be accurately positioned.

According to the embodiment of the present disclosure, the fluid control device capable of performing accurate positioning can be provided.

DETAILED DESCRIPTION OF THE DISCLOSURE

An embodiment is described below.

In the accompanying drawings, components illustrated may be enlarged for facilitating the understanding. The dimensional ratios of the components may differ from real ones or ones in a different drawing. In the cross-sectional views, hatching on some of the components may be omitted for facilitating the understanding.

Figures 1A, 1B:
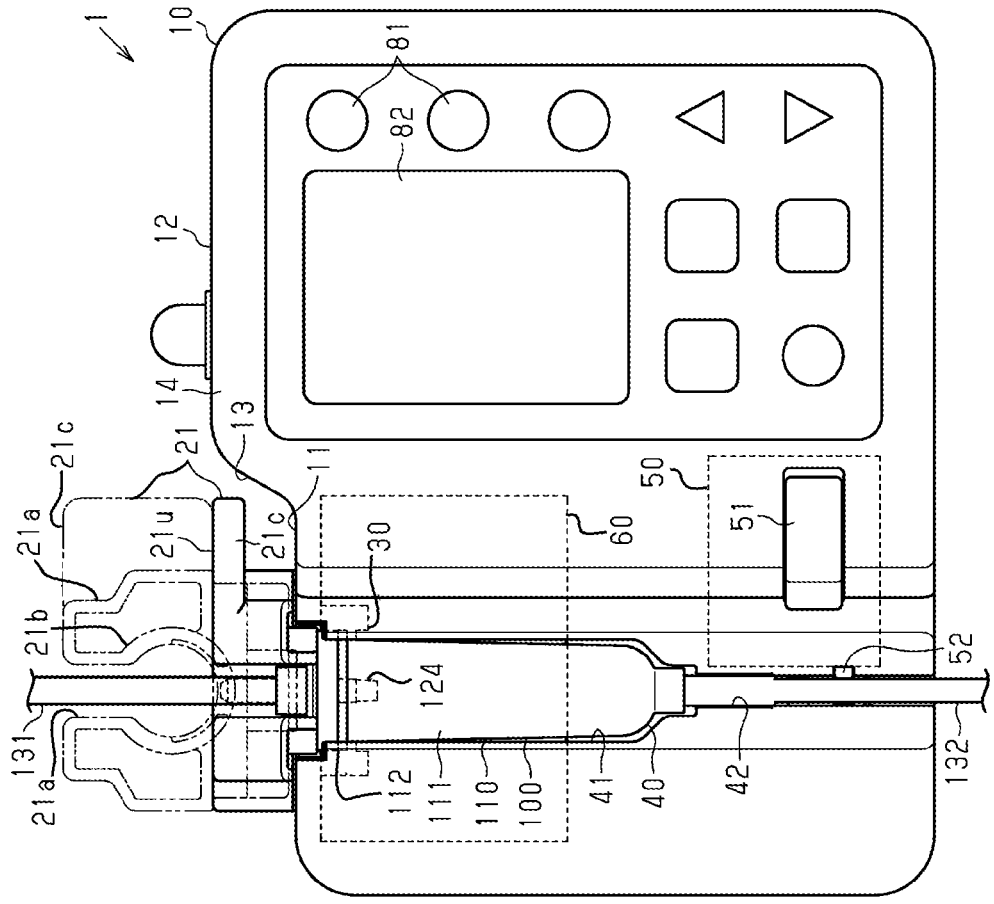
FIG. 1A is a schematic front view of a fluid control device.
FIG. 1B is a left side view of the fluid control device.
Figure 2:
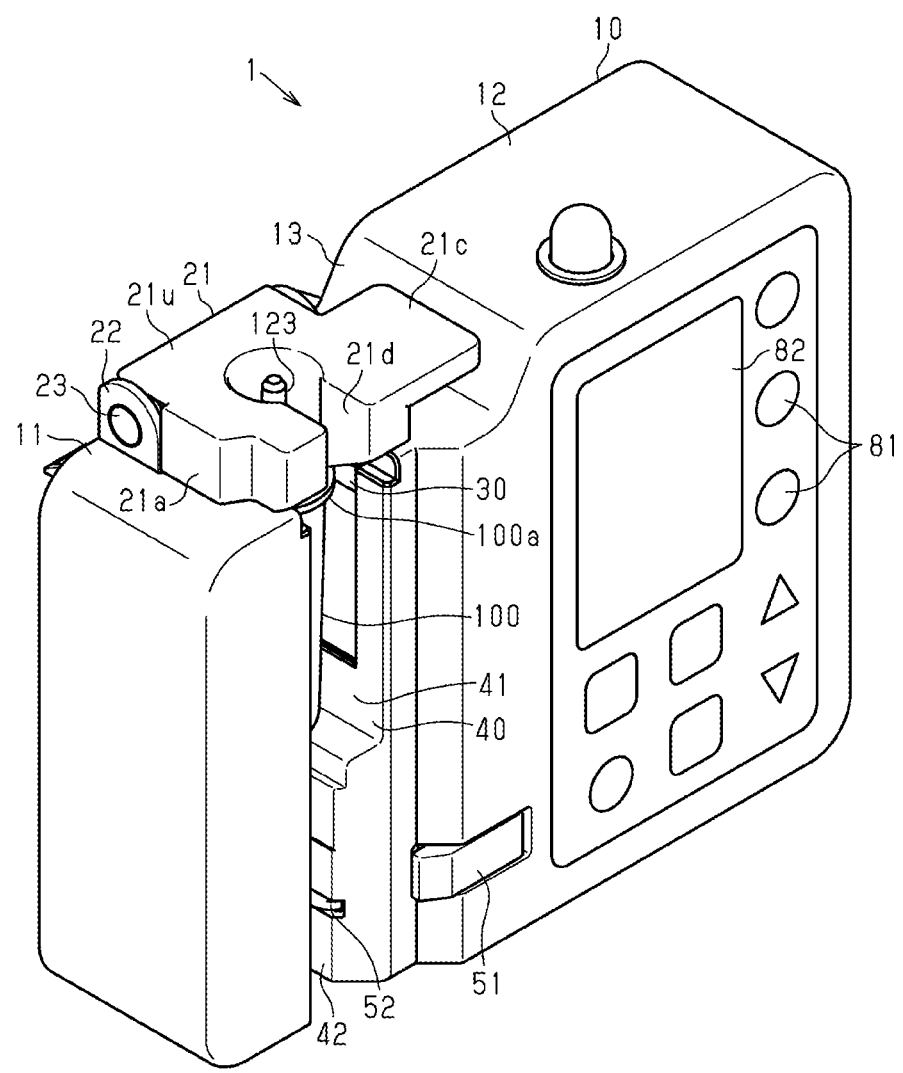
FIG. 2 is a schematic perspective view of the fluid control device.

As illustrated in FIGS. 1A, 1B, and 2, a fluid control device 1 has a substantially rectangular parallelepiped shape. The fluid control device 1 may be attached to, for example, a transfusion stand or the like. A casing 10 of the fluid control device 1 is uneven in its upper portion and has a first upper surface 11, a second upper surface 12, and a coupling oblique surface 13 between the first upper surface 11 and the second upper surface 12. In the casing 10, the second upper surface 12 is higher than the first upper surface 11.

The fluid control device 1 includes a flap 21 as a third fixation section. The flap 21 is arranged on the first upper surface 11.

As illustrated in FIGS. 1A and 1B, the flap 21 is pivotably supported by a support section 22 and a support shaft 23 at the rear end of the upper surface of the casing 10. The support shaft 23 is arranged along the rear end of the casing 10. Accordingly, the flap 21 is pivotable in the front and rear direction of the casing 10. The flap 21 is urged frontward by an elastic member (e.g., a spring), which is not illustrated. In FIGS. 1A and 1B, the flap 21 pivoted to the rear side is indicated by a dash-dot-dot line. The position of the flap 21 indicated by a solid line is referred to as a first position. The position of the flap 21 indicated by the dash-dot-dot line is referred to as a second position. That is, the flap 21 is switchable between the first position and the second position. In the first position, the upper surface of the flap 21 is flush with the second upper surface 12 of the casing 10. In the present specification, "flush with" includes being flush with and being substantially flush with. Two surfaces being flush with each other indicate the two surfaces being flush with each other at least in part.

As illustrated in FIGS. 1A, 3, 7A, and 7B, the flap 21 includes a base section 21a through which the support shaft 23 is inserted, a pressing section 21b at the center of the base section 21a, and an operation section 21c extending from the base section 21a toward the coupling oblique surface 13, which is positioned in a central side of the casing 10. The pressing section 21b has a cylindrical shape in which its side surface is cut along its central axis, and that cut section 21d is positioned on a side corresponding to a front surface 14 of the casing 10.

As illustrated in FIGS. 1A and 1B, when the operation section 21c is pressed in an upward and rearward direction in an arc shape around the support shaft 23 for the flap 21, the flap 21 is pivoted toward the rear. The flap 21 is pivoted toward the front by the elastic member.

The fluid control device 1 includes an operation section 81 and a display section 82 in the right portion of the casing 10 and includes a housing section 40 in the left portion of the casing 10. The operation section 81 is operated to perform the settings for operations of the fluid control device 1 (various conditional settings) or the like. Statuses or the like of the fluid control device 1 are displayed on the display section 82.

Figure 5:
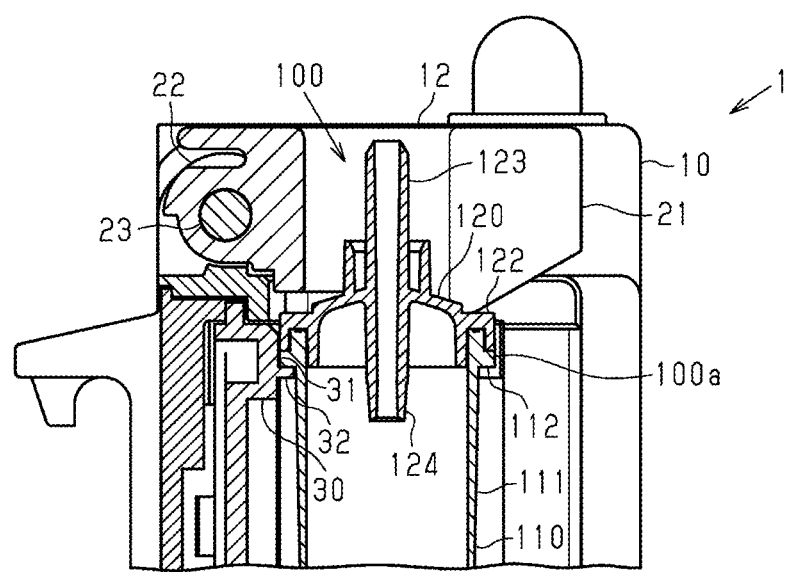
FIG. 5 is a partial schematic cross-sectional view of the fluid control device.
Figure 6:
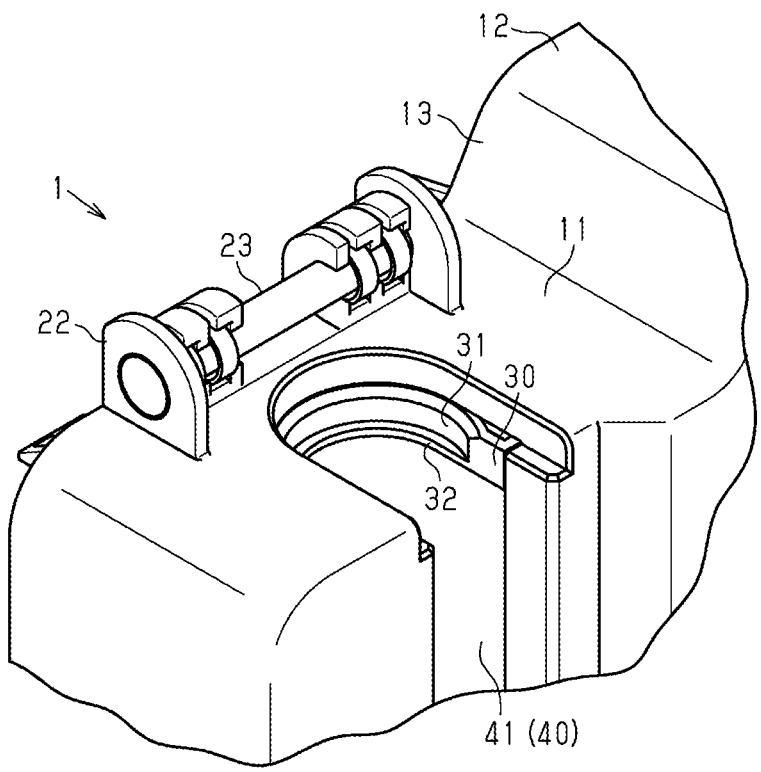
FIG. 6 is a partial enlarged perspective view of the fluid control device.
Figure 7A:
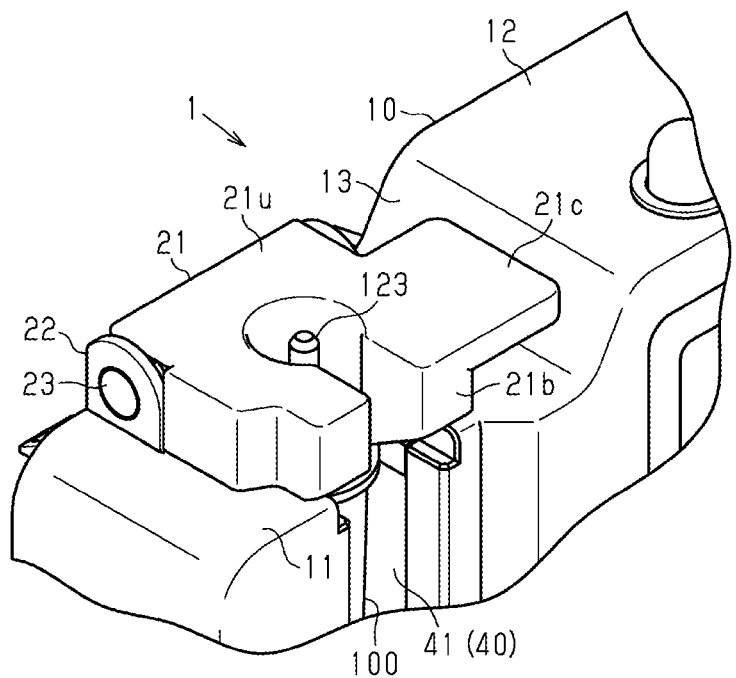
FIGS. 7A and 7B are schematic perspective views that illustrate fixation of an infusion tube.
Figure 7B:
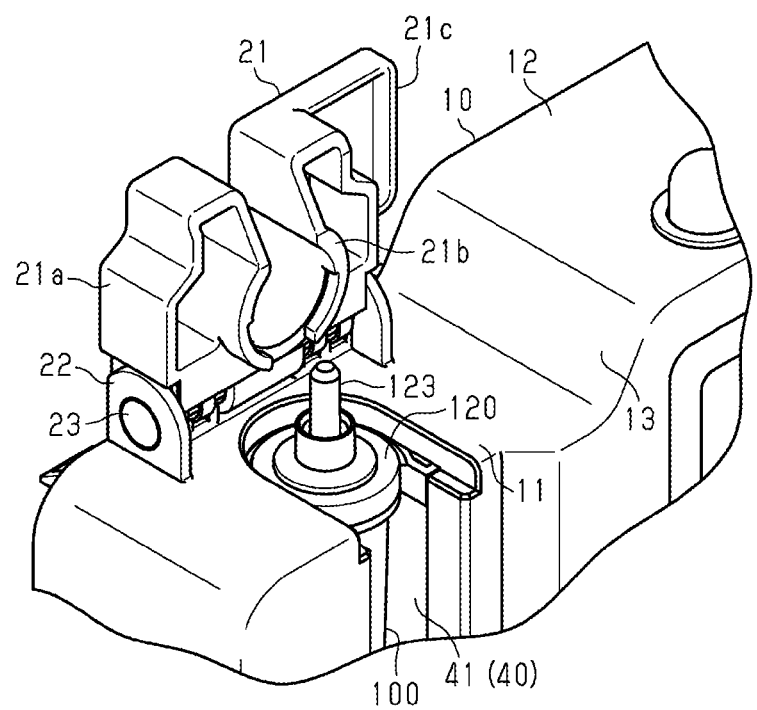

As illustrated in FIGS. 1A, 2, and 5, the housing section 40 houses an infusion tube 100. The infusion tube 100 includes a tube main body 110 and a cap 120. The tube main body 110 allows the predetermined light to pass therethrough. The tube main body 110 includes a tube section 111 and a flange section 112 at the upper end portion of the tube section 111. The tube section 111 is tubular, and it is approximately cylindrical in the present embodiment. The flange section 112 protrudes outward from the tube section 111 when the tube section 111 is seen in the longitudinal direction. From the approximately cylindrical tube section 111, the flange section 112 protrudes outward in the diameter direction of the tube section 111. The tube main body 110 includes a connection pipe at the lower end of the tube section 111, and a transport tube 132 is attached to that connection pipe. The transport tube 132 is connected to an infusion needle (not illustrated).

The cap 120 is attached to the upper end of the tube main body 110. The cap 120 closes an opening at the upper end of the tube main body 110. The cap 120 includes a fixation section 122 fixed to the upper end of the tube main body 110. The fixation section 122 and the flange section 112 in the tube main body 110 constitute a flange 100a in the infusion tube 100. The flange 100a protrudes outward as seen in the longitudinal direction of the tubular infusion tube 100.

The cap 120 includes a connection pipe 123 extending upward, and the connection pipe 123 is connected to a transport tube 131 (see FIGS. 1A and 1B). The transport tube 131 is connected to a transfusion pack (not illustrated), and fluid is supplied from that transfusion pack through the transport tube 131 to the infusion tube 100. The cap 120 includes a nozzle 124 capable of being inserted inside the tube main body 110. Fluid flowing through the transport tube 131 drips from the end (lower end) of that nozzle 124 as droplets.

The housing section 40 includes a tube housing section 41 for housing the infusion tube 100 and a pipe insertion section 42 in which the transport tube 132 connected to the infusion tube 100 can be inserted.

As illustrated in FIG. 1A, the fluid control device 1 includes a pipe fixation section 50 and a droplet detecting section 60. The pipe fixation section 50 fixes the transport tube 132 inserted in the pipe insertion section 42. The pipe fixation section 50 includes an operation member 51 and a fixation member 52. The operation member 51 is exposed to the front of the casing 10 and is supported movably in the left and right direction. The fixation member 52 is supported movably in a direction perpendicular to the transport tube 132 inserted in the pipe insertion section 42 (left and right direction of the casing 10 in the present embodiment). The pipe fixation section 50 is configured to urge each of the operation member 51 and the fixation member 52 toward the transport tube 132 by an elastic member (e.g., a spring), which is not illustrated. The pipe fixation section 50 is configured to move the fixation member 52 in a direction remote from the transport tube 132 (rightward in the present embodiment) by an operation by an operator on the operation member 51 (rightward movement).

The droplet detecting section 60 detects a droplet dripping from the nozzle 124 in the infusion tube 100 and calculates the amount of droplets.

Figure 9:
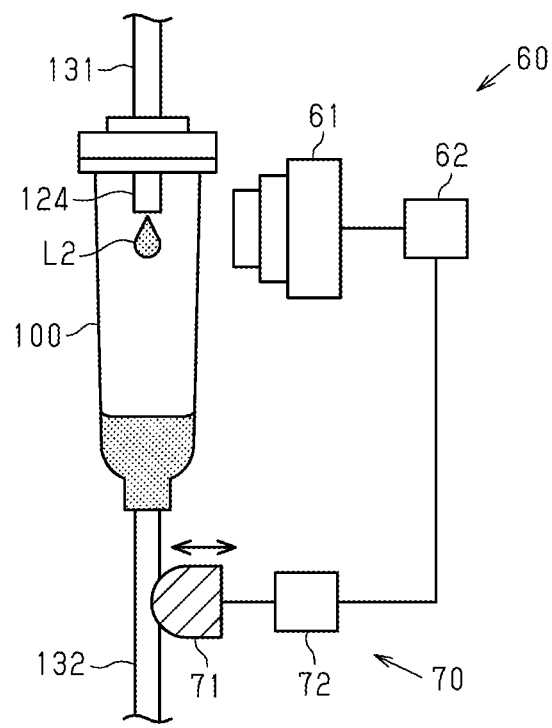
FIG. 9 is a schematic block diagram that illustrates droplet measurement and fluid control.
Figure 10A:
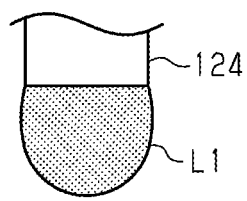
FIG. 10A is an illustration of a droplet at a lower end of a nozzle.
Figure 10B:
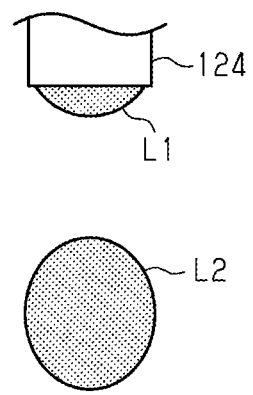
FIG. 10B is an illustration of a droplet dropping from the nozzle.

FIG. 9 is a partial block diagram of the fluid control device 1 and illustrates an example configuration of the droplet detecting section 60. The droplet detecting section 60 includes a camera 61 as an optical sensor and a data processing section 62. An example of the camera 61 may be a two-dimensional image sensor. The camera 61 is arranged so as to capture an image of a region including the lower end of the nozzle 124 and outputs image data. FIG. 10A illustrates an example of image data of a droplet L1 growing at the lower end of the nozzle 124 obtained by the camera 61. FIG. 10B illustrates an example of image data of a droplet L2 dropping from the nozzle 124 obtained by the camera 61.

The data processing section 62 calculates the amount of drips based on a plurality of image data elements obtained by the camera 61. For example, the data processing section 62 creates a circle corresponding to (fitted to) a droplet at the lower end of the nozzle 124 based on image data. It can estimate the volume of the droplet from a change in the radius of that circle. It can count the number of drips from a change in the center position of that circle. It can calculate the amount of drips from the volume of the droplet and the counted value (the number of drips per unit time).

FIG. 9 illustrates an example configuration of an adjustment section 70. The adjustment section 70 adjusts pressing on the transport tube 132 based on the amount of drips calculated by the droplet detecting section 60. The adjustment section 70 includes a pressing member 71 and a control section 72. The pressing member 71 is positioned near the side of the transport tube 132 and is movable in a direction in which it comes into contact with or becomes remote from the transport tube 132. The transport tube 132 is a soft tube made of a flexible material, such as a resin. The control section 72 controls the pressing member 71 based on the amount of drips of droplets. For example, when the amount of drips is larger than a set value, the pressing member 71 is controlled to increase the quantity of narrowing the transport tube 132. In contrast, when the amount of drips is smaller than the set value, the pressing member 71 is controlled to decrease the quantity of narrowing the transport tube 132. The quantity of flow of fluid flowing through the transport tube 132 can be controlled by the quantity of narrowing the transport tube 132.

Figure 11:
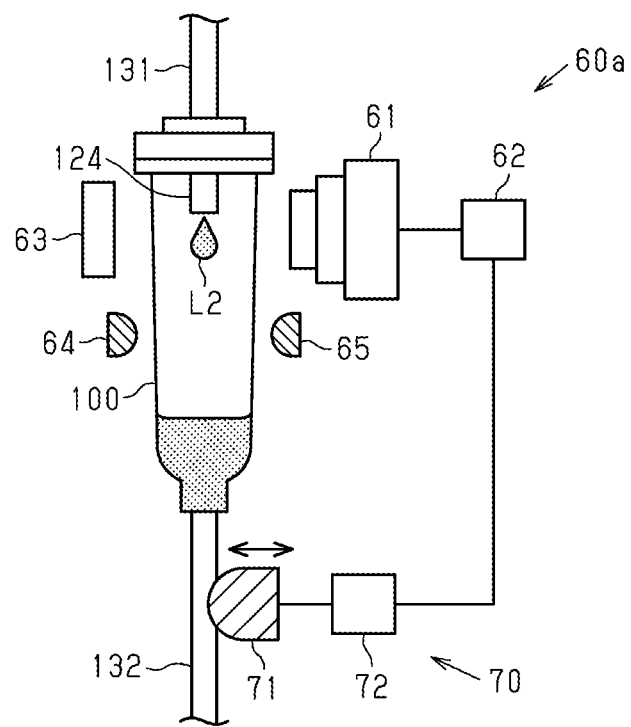
FIG. 11 is a schematic block diagram that illustrates droplet measurement and fluid control in a variation.

FIG. 11 is a schematic block diagram of a droplet detecting section 60a in a variation. The variation includes an illuminator 63. One example of the illuminator 63 may be a light-emitting diode and illuminates a droplet on the lower end of the nozzle 124. The use of the illuminator 63 can reduce effects from disturbance, such as outside light, and enable capturing a clear image of the droplet L1 and calculating the amount of droplets with high accuracy.

The droplet detecting section 60a illustrated in FIG. 11 includes a light emitting section 64 (e.g., light-emitting diode) and a light receiving section 65 (e.g., phototransistor). The light emitting section 64 emits light capable of passing through the infusion tube 100. The light receiving section 65 is arranged so as to receive the light emitted from the light emitting section 64. The light emitted from the light emitting section 64 is blocked by a droplet dropping inside the infusion tube 100. Accordingly, drips can be counted in the light receiving section 65 from a change in the amount of light received. The light receiving section 65 may be arranged so as to receive the light reflected from a dropping droplet.

Figure 3:
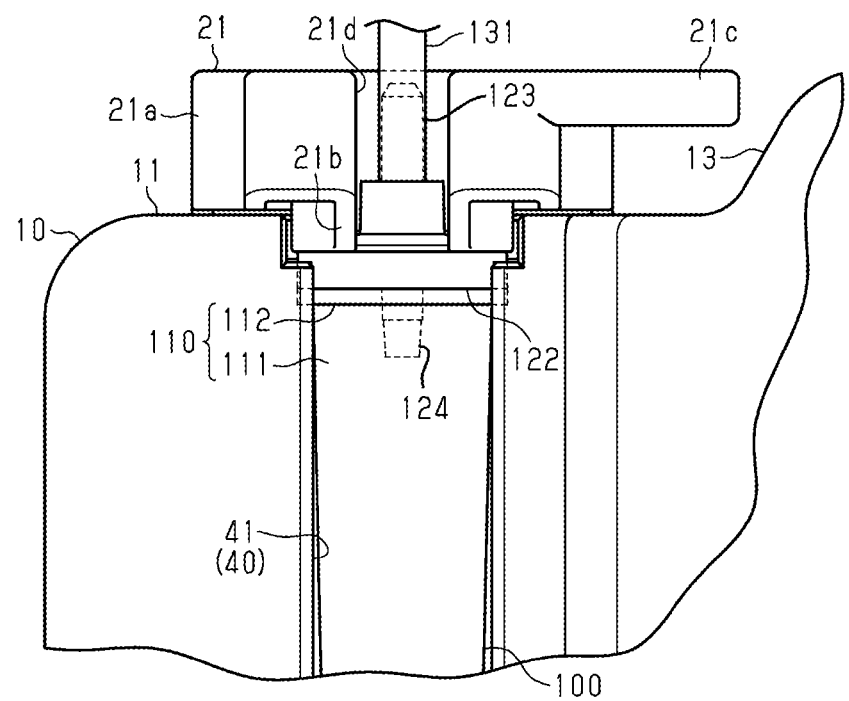
FIG. 3 is a partial enlarged front view of the fluid control device.
Figure 4:
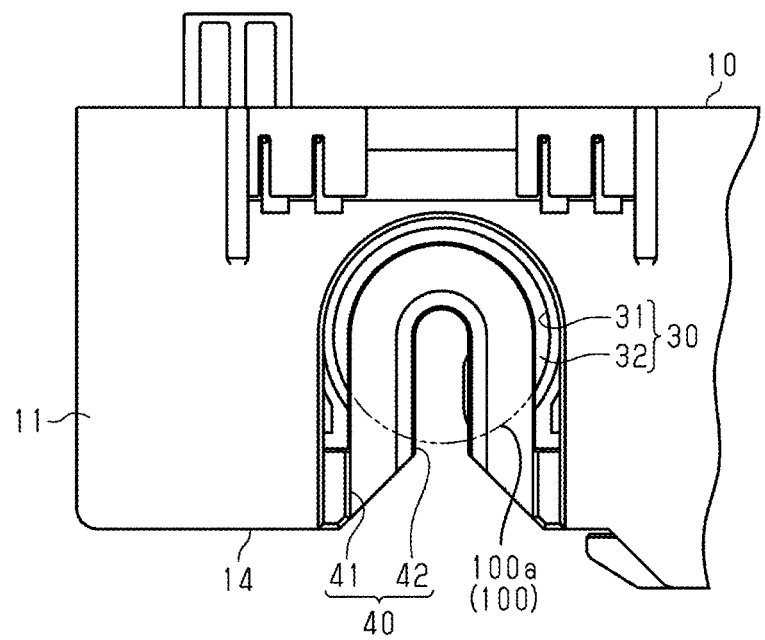
FIG. 4 is a partial enlarged plan view of the fluid control device.

As illustrated in FIGS. 3, 4, 5, and 6, the casing 10 includes an engagement member 30, and the engagement member 30 is fixed in the casing 10. In FIG. 1A, the outline of the engagement member 30 is indicated by the broken line. As illustrated in FIG. 4, the engagement member 30 has a U shape opened to the front side of the casing 10 (downward in FIG. 4). The housing section 40 in the casing 10 has an opening whose width is substantially the same as that of the opening of the engagement member 30. These openings allow the tube section 111 in the tube main body 110 in the infusion tube 100 to be inserted therethrough. Furthermore, the casing 10 and the engagement member 30 are disposed so as not to allow the flange 100a in the infusion tube 100 to be inserted therethrough along the front and rear direction of the casing 10.

Specifically, as illustrated in FIG. 4, the engagement member 30 has a fixation surface 31 allowing the flange 100a (indicated by the dash-dot-dot line) in the infusion tube 100 to be inserted in the longitudinal direction of the infusion tube 100 (being the height direction of the casing 10 and the direction of the front and back sides of FIG. 4). The fixation surface 31 has a C shape as seen from the first upper surface 11 of the casing 10, and the distance between the opposite end portions of the fixation surface 31 is smaller than the diameter of the flange 100a in the infusion tube 100 and larger than the diameter of the tube section 111. The engagement member 30 includes a flange 32 protruding from the fixation surface 31 toward the inside. The flange 32 allows the tube section 111 in the infusion tube 100 to be inserted along the front and rear direction of the casing 10 (vertically in FIG. 4).

As illustrated in FIG. 3, the flange 32 in the engagement member 30 engages with the flange 100a in the infusion tube 100 in a direction along the longitudinal direction of the infusion tube 100 (vertically in FIG. 3) and regulates downward movement of the flange 100a, that is, the infusion tube 100. That is, the flange 32 in the engagement member 30 locks the infusion tube 100 in the direction along the longitudinal direction of the infusion tube 100. That flange 32 is an example of a first fixation section.

As illustrated in FIG. 4, the fixation surface 31 of the engagement member 30 engages with the flange 100a in the infusion tube 100 in a direction orthogonal to the longitudinal direction of the infusion tube 100 and regulates movement of the flange 100a, that is, the infusion tube 100 toward the direction orthogonal to the longitudinal direction. That is, the fixation surface 31 of the engagement member 30 fixes the infusion tube 100 in the direction orthogonal to the longitudinal direction of the infusion tube 100. That fixation surface 31 of the engagement member 30 is one example of a second fixation section.

As illustrated in FIG. 3, the flap 21 includes the pressing section 21b, which can be inserted in the housing section 40 in the casing 10. The pressing section 21b can be in contact with the cap 120 in the infusion tube 100 housed in the housing section 40. The flap 21 urges the infusion tube 100 downward by the pressing section 21b brought into with the cap 120 by an elastic member.

In the present embodiment, the engagement member 30 is integrated with a unit in the droplet detecting section 60 (camera unit). The droplet detecting section 60 includes a frame to which the camera 61 is attached, and the frame is fixed to the casing 10. The engagement member 30 is attached to the frame or is formed integrally with the frame. Thus, the position of the engagement member 30, that is, the position of the infusion tube 100 fixed by the engagement member 30 is relatively determined with respect to the image capture position of the camera 61.

Figure 8:
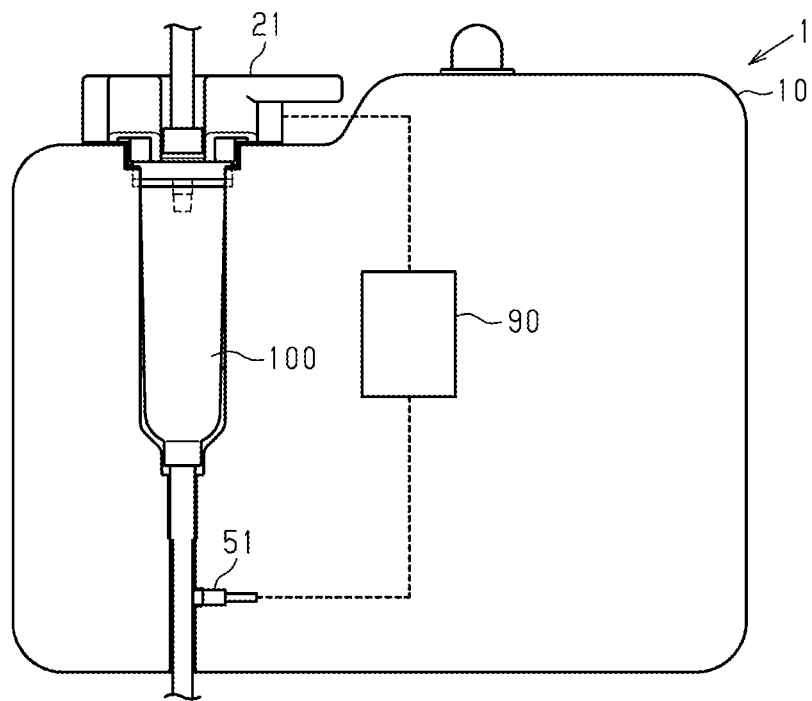
FIG. 8 is a schematic block diagram that illustrates interlocking between a flap and a fixation member.

As illustrated in FIG. 8, the fluid control device 1 includes an interlocking mechanism 90. The interlocking mechanism 90 moves the fixation member 52 in response to pivoting of the flap 21. Specifically, when the flap 21 is in the first position where it presses the first upper surface 11 of the casing 10 or the cap 120 in the infusion tube 100 by the elastic force of the elastic member (the position indicated by the solid line in FIGS. 1A and 1B), the interlocking mechanism 90 moves the fixation member 52 such that the fixation member 52 protrudes into the pipe insertion section 42. When the flap 21 is pivoted to the second position, which is indicated by the dash-dot-dot line in FIGS. 1A and 1B, by an operation of pivoting the flap 21 toward the rear, the interlocking mechanism 90 moves the fixation member 52 such that the fixation member 52 does not protrude into the pipe insertion section 42.

As the interlocking mechanism 90, a mechanical mechanism, an electrical mechanism, an electrical and mechanical mechanism, and the like can be used. As examples of the mechanical mechanism, a gear mechanism, a cam mechanism, a rack-and-pinion mechanism, and the like can be used, and a mechanism for transmitting pivoting of the flap 21 and for converting it into straight movement and moving the fixation member 52 can be used. As an example of the electrical mechanism, a mechanism for detecting pivoting of the flap 21 by a photoelectrical sensor of the light-shielding type or reflection type and moving the fixation member 52 based on the detection by a linear actuator or the like can be used. As an example of the electrical and mechanical mechanism, a mechanism for transmitting pivoting of the flap 21 by using a gear, a cam, or the like, switching on or off a switch or the like, and moving the fixation member 52 based on the on or off of the switch by a linear actuator or the like can be used.

(Operations)

As illustrated in FIGS. 1A and 1B, the fluid control device 1 includes the casing 10 configured to house the cylindrical infusion tube 100 and the droplet detecting section 60 configured to detect the amount of droplets dripping from the nozzle 124 in the infusion tube 100 housed in the casing 10. The casing 10 includes the engagement member 30. The engagement member 30 includes the flange 32 configured to engage with the flange 100a in the infusion tube 100 in the direction along the longitudinal direction of the infusion tube 100 and fix the infusion tube, and the fixation surface 31 configured to fix the infusion tube 100 in the direction orthogonal to the longitudinal direction of the infusion tube 100.

The infusion tube 100 includes the flange 100a protruding outward in the diameter direction. The flange 100a in the infusion tube 100 engages with the flange 32 in the engagement member 30 in the direction along the longitudinal direction of the infusion tube 100. In that way, the position of the infusion tube 100 in the longitudinal direction is fixed by the flange 32 in the engagement member 30. The flange 100a in the infusion tube 100 is positioned by the fixation surface 31 of the engagement member 30 in the direction orthogonal to the longitudinal direction of the infusion tube 100. Thus, the infusion tube 100 can be positioned more accurately, for example, in comparison with the configuration in which it is maintained by clamping of the tube section 111 in the infusion tube 100.

The droplet detecting section 60 includes the camera 61 and the data processing section 62. The camera 61 is arranged so as to capture an image of a region including the lower end of the nozzle 124 and outputs image data. If the infusion tube 100 is misaligned in the direction along its longitudinal direction, a droplet may deviate from the image capture area of the camera 61. If the infusion tube 100 is misaligned in the direction orthogonal to its longitudinal direction, a droplet may deviate from the image capture area of the camera 61 or the blurred image data of out-of-focus droplet may be obtained. In those cases, the calculated volume of the droplet may have an error, and the error may be large.

As previously described, in the fluid control device 1 in the present embodiment, the infusion tube 100 is positioned in the direction along the longitudinal direction of the infusion tube 100 and in the direction orthogonal to the longitudinal direction. Thus, droplets can be contained in the image capture area of the camera 61. In addition, clear image data of droplets can be obtained. Therefore, an error is less likely to occur in the volume of the droplet or the error can be reduced. Accordingly, the amount of droplets can be controlled more precisely.

The fluid control device 1 includes the flap 21. The flap 21 is switchable between the first position, which is indicated by the solid line in FIGS. 1A and 1B and illustrated in FIG. 7A, and the second position, which is indicated by the dash-dot-dot line in FIGS. 1A and 1B and illustrated in FIG. 7B.

The flap 21 arranged in the first position partially covers the upper surface of the infusion tube 100 housed in the housing section 40 in the casing 10. Accordingly, the flap 21 in the first position regulates upward movement of the infusion tube 100. That flap 21 fixes the position of the infusion tube 100.

The flap 21 arranged in the second position does not cover the upper surface of the infusion tube 100 housed in the housing section 40. Accordingly, the flap 21 in the second position permits upward movement of the infusion tube 100. Thus, the casing 10 can be easily attached and detached. Specifically, the flange 100a in the infusion tube 100 is positioned in the direction orthogonal to the longitudinal direction of the infusion tube 100 by the fixation surface 31 of the engagement member 30. The tube section 111 in the infusion tube 100 can be inserted along the front and rear direction of the casing 10 (vertically in FIG. 4). Accordingly, after the infusion tube 100 is moved upward up to a position where the flange 100a does not engage with the fixation surface 31 of the engagement member 30, the infusion tube 100 is moved toward the front side of the casing 10. In that way, the infusion tube 100 can be extracted from the fluid control device 1. To attach the infusion tube 100, it may be moved in the way opposite to the above-described way.

The flap 21 is urged frontward by an elastic member (e.g., a spring), which is not illustrated. Accordingly, the flap 21 automatically moves from the second position to the first position by the elastic member. In the first position, the flap 21 fixes the infusion tube 100 housed in the housing section 40 in the casing 10. In the present embodiment, the flap 21 is brought into contact with the infusion tube 100 housed in the housing section 40 in the casing 10 by the elastic member (not illustrated). Because the flap 21 presses the flange 100a in the infusion tube 100 to the flange 32 in the engagement member 30, the positioning can be stabilized. The flap 21 and the flange 32 in the engagement member 30 hold the flange 100a in the infusion tube 100 therebetween. Accordingly, the misalignment after the infusion tube 100 is attached can be suppressed.

The flap 21 is supported by the support shaft 23 extending along the rear end of the first upper surface 11 of the casing 10 and is pivotable in the front and rear direction of the casing 10. The flap 21 has the cut section 21d in its front surface. The cut section 21d enables pivoting of the flap 21 without bending of the transport tube 131 connected to the infusion tube 100.

The engagement member 30 has the U shape opened toward the front of the casing 10 (downward in FIG. 4). The housing section 40 in the casing 10 has the opening whose width is substantially the same as that of the opening of the engagement member 30. These openings allow the tube section 111 in the tube main body 110 in the infusion tube 100 to be inserted therethrough. Accordingly, in the state where the flange 100a in the infusion tube 100 is higher than the first upper surface 11 of the casing 10, the tube section 111 in the infusion tube 100 is inserted into the engagement member 30. After that, the infusion tube 100 is moved downward along its longitudinal direction, and the infusion tube 100 can be easily housed in the housing section 40.

The droplet detecting section 60 includes the camera 61 configured to optically catch a droplet dripping from the nozzle 124. The droplet detecting section 60 can calculate the volume of the droplet based on the image data obtained by the camera 61 and can determine the amount of droplets.

The camera 61 is fixed to the frame member, and the engagement member 30 is arranged integrally with the frame member. Accordingly, the relative misalignment between the camera 61 and the engagement member 30, that is, between the camera 61 and the infusion tube 100, which is positioned by the engagement member 30, can be suppressed.

When the flap 21 is in the first position, where it presses the first upper surface 11 of the casing 10 or the cap 120 in the infusion tube 100 by the elastic force of the elastic member, an upper surface 21u of the flap 21 is flush with the second upper surface 12 of the casing 10. For example, if the fluid control device 1 falls, the impact of the fall or the like on the flap 21 can be softened because the flap 21 and the second upper surface 12 are flush with each other, and the damage to the flap 21 can be reduced.

The flap 21 does not allow the connection pipe 123 in the housed infusion tube 100 to protrude from the upper surface 21u of the flap 21. Thus, the connection portion (connection pipe 123) of the infusion tube 100 and the transport tube 131 can be prevented from being hit by an object or the like.

As described above, the present embodiment can provide advantages below.

(1) The fluid control device 1 includes the casing 10 configured to house the tubular infusion tube 100 and the droplet detecting section 60 configured to detect the amount of droplets dripping from the nozzle 124 in the infusion tube 100 housed in the casing 10. The infusion tube 100 includes the flange 100a protruding outward. The casing 10 includes the engagement member 30. The engagement member 30 includes the flange 32 configured to engage with the flange 100a in the infusion tube 100 in the direction along the longitudinal direction of the infusion tube 100 and fix the infusion tube and the fixation surface 31 configured to fix the infusion tube 100 in the direction orthogonal to the longitudinal direction of the infusion tube 100. The flange 100a in the infusion tube 100 and the engagement member 30 enable more precise positioning of the infusion tube 100.

(2) In the fluid control device 1, the infusion tube 100 is positioned in the direction along the longitudinal direction of the infusion tube 100 and in the direction orthogonal to the longitudinal direction. Thus, droplets can be contained in the image capture area of the camera 61. In addition, clear image data of droplets can be obtained. Therefore, an error is less likely to occur in the volume of the droplet or the error can be reduced. Accordingly, the amount of droplets can be controlled more precisely.

(3) The fluid control device 1 includes the flap 21. The flap 21 is pivotably supported on the upper surface of the casing 10 and can be brought into contact with the infusion tube housed in the casing 10 by the elastic member (not illustrated). Because the flap 21 presses the flange 100a in the infusion tube 100 to the flange 32 in the engagement member 30, the positioning can be stabilized. The flap 21 and the flange 32 in the engagement member 30 hold the flange 100a in the infusion tube 100 therebetween. Accordingly, the misalignment after the infusion tube 100 is attached can be suppressed.

(4) The flap 21 is supported by the support shaft 23 extending along the rear end of the first upper surface 11 of the casing 10 and is pivotable in the front and rear direction of the casing 10. The flap 21 has the cut section 21d in its front surface. The cut section 21d enables pivoting of the flap 21 without bending of the transport tube 131 connected to the infusion tube 100.

(5) The engagement member 30 has the U shape opened toward the front of the casing 10 (downward in FIG. 4). The housing section 40 in the casing 10 has the opening whose width is substantially the same as that of the opening of the engagement member 30. These openings allow the tube section 111 in the tube main body 110 in the infusion tube 100 to be inserted therethrough. Accordingly, in the state where the flange 100a in the infusion tube 100 is higher than the first upper surface 11 of the casing 10, the tube section 111 in the infusion tube 100 is inserted into the engagement member 30. After that, the infusion tube 100 is moved downward along its longitudinal direction, and the infusion tube 100 can be easily housed in the housing section 40.

(6) The droplet detecting section 60 includes the camera 61 configured to optically catch a droplet dripping from the nozzle 124. The droplet detecting section 60 can calculate the volume of the droplet based on the image data obtained by the camera 61 and can determine the amount of droplets.

(7) The camera 61 is fixed to the frame member, and the engagement member 30 is arranged integrally with the frame member. Accordingly, the relative misalignment between the camera 61 and the engagement member 30, that is, between the camera 61 and the infusion tube 100, which is positioned by the engagement member 30, can be suppressed.

(8) When the flap 21 is in the first position, where it presses the first upper surface 11 of the casing 10 or the cap 120 in the infusion tube 100 by the elastic force of the elastic member, the upper surface 21u of the flap 21 is flush with the second upper surface 12 of the casing 10. For example, if the fluid control device 1 falls, the impact of the fall or the like on the flap 21 can be softened because the flap 21 and the second upper surface 12 are flush with each other, and the damage to the flap 21 can be reduced.

(9) The flap 21 does not allow the connection pipe 123 in the housed infusion tube 100 to protrude from the upper surface 21u of the flap 21. Thus, the connection portion (connection pipe 123) of the infusion tube 100 and the transport tube 131 can be prevented from being hit by an object or the like.

The above-described embodiment may be carried out in the following modes.

In the above-described embodiment, the flange section 112 in the tube main body 110 and the fixation section 122 in the cap 120 constitute the flange 100a in the infusion tube 100, which is held between the engagement member 30 and the flap 21. In another example, a flange may be disposed on either one of the tube main body 110 and the cap 120, and the flange may be held between the engagement member 30 and the flap 21 to fix the infusion tube 100.

The direction of pivoting of the flap 21 in the above-described embodiment may be changed. For example, the flap 21 may be pivotable in the left and right direction of the casing 10.

In the above-described embodiment, the infusion tube 100 is pressed by the flap 21. The infusion tube 100 may be pressed by other configurations. For example, the third fixation section capable of sliding along the first upper surface 11 of the casing 10 may be included.

In the above-described embodiment, the infusion tube 100 is pressed by the flap 21. When upward movement of the infusion tube 100 can be regulated, the flap 21 in the first position may be in a state where it is not in direct contact with the upper surface of the infusion tube 100.

Technical idea that can be derived from the above-described embodiment is described below.

A fluid control device being an embodiment of the present disclosure includes a casing configured to house a tubular infusion tube including a nozzle from which fluid drips and a droplet detecting section configured to detect an amount of droplets dripping from the nozzle in the infusion tube housed in the casing. The infusion tube includes a flange protruding outward. The casing includes a first fixation section configured to engage with the flange in a direction along a longitudinal direction of the infusion tube and fix the infusion tube and a second fixation section configured to fix the infusion tube in a direction orthogonal to the longitudinal direction of the infusion tube.

According to that configuration, the infusion tube is fixed in the longitudinal direction of the infusion tube by the first fixation section, is fixed in the direction orthogonal to the longitudinal direction by the second fixation section, and is thus positioned accurately.

The above-described fluid control device may preferably further include a third fixation section switchable between a first position where it regulates upward movement of the infusion tube and a second position where it permits the upward movement of the infusion tube.

According to that configuration, the infusion tube is accurately positioned by the third fixation section arranged in the first position. When the third fixation section is arranged in the second position, the infusion tube can be easily attached and detached.

In the above-described fluid control device, the third fixation section may preferably be a flap pivotably supported on an upper surface of the casing and capable of being in contact with an upper portion of the infusion tube housed in the casing, and the flap and the first fixation section may preferably hold the flange in the infusion tube therebetween.

According to that configuration, the positioning may be more accurate.

In the above-described fluid control device, the third fixation section may preferably be supported by a support shaft extending along a rear end of the upper surface of the casing, be pivotable in a front and rear direction of the casing, and have a cut section in its front surface.

In the above-described fluid control device, the upper surface of the casing may preferably include a first upper surface and a second upper surface being higher than the first upper surface, the third fixation section may preferably be arranged on the first upper surface, and an upper surface of the third fixation section in the first position may preferably be flush with the second upper surface.

According to that configuration, the force placed on the second upper surface and the third fixation section is split, and the damage to the third fixation section is reduced.

In the above-described fluid control device, the droplet detecting section may preferably include a camera configured to capture an image of a droplet dripping from the nozzle.

According to that configuration, the images of the droplets dripping from the nozzle can be reliably captured by the camera.

The above-described fluid control device may preferably further include a frame member arranged inside the casing and to which the camera is attached, and the first fixation section and the second fixation section may preferably be arranged integrally with the frame member.

According to that configuration, the relative misalignment among the camera, the first fixation section, and the second fixation section can be suppressed.

In the fluid control device according to some non-limiting examples, the infusion tube can include the nozzle for allowing droplets to drop downward inside the infusion tube and a diameter-direction outward projecting section protruding from an outward side surface of the infusion tube. The diameter-direction outward projecting section in the infusion tube may be a single planar flange or may be composed of a plurality of projections. The first fixation section can be configured as a seat capable of being in direct contact with the lower surface of the diameter-direction outward projecting section in the infusion tube and supporting the lower surface of the diameter-direction outward projecting section in the infusion tube from below. The first fixation section may be configured as a flat upper surface capable of having surface contact with the lower surface of the diameter-direction outward projecting section in the infusion tube. The first fixation section may be configured to support a plurality of first predetermined locations spaced from each other in the circumferential direction of the lower surface of the diameter-direction outward projecting section in the infusion tube from below. The first fixation section may be configured as a plurality of first support surfaces or a plurality of first support points aligned on an imaginary plane parallel with or coinciding with the lower surface of the diameter-direction outward projecting section in the infusion tube.

In the fluid control device according to some non-limiting examples, the casing in the fluid control device can include the pipe insertion section for housing a portion of a predetermined-length of the flexible transport tube connected to the lower portion of the infusion tube. The pipe insertion section can be a linear groove configured to allow the predetermined length portion of the flexible transport tube to extend linearly in a predetermined extending direction that can be the downward direction. The first fixation section can be configured to expand over an imaginary plane where the first fixation section is orthogonal to the longitudinal direction of the linear groove or configured as a plurality of sections aligned on that imaginary plane.

In the fluid control device according to some non-limiting examples, the diameter-direction outward projecting section in the infusion tube can have a diameter-direction outward surface being the outermost surface of the infusion tube, and the second fixation section may be configured as a diameter-direction inward surface capable of being in direct contact with the diameter-direction outward surface of the diameter-direction outward projecting section in the infusion tube. The diameter-direction outward projecting section in the infusion tube can have a diameter-direction outward projecting curved surface, and the second fixation section may be configured as a depressed curved surface capable of having surface contact with the diameter-direction outward projecting curved surface of the diameter-direction outward projecting section in the infusion tube. The second fixation section may be configured as a plurality of second support surfaces or a plurality of second support points laterally supporting a plurality of predetermined locations spaced from each other in the circumferential direction in the diameter-direction outward surface of the flange in the infusion tube.

In the fluid control device according to some non-limiting examples, the first fixation section and the second fixation section can be configured to work together, to virtually horizontally maintain the lower surface of the diameter-direction outward projecting section in the infusion tube, and to virtually vertically maintain the diameter-direction outward surface of the diameter-direction outward projecting section in the infusion tube.

1 fluid control device, 10 casing, 21 flap, 30 engagement member, 31 fixation surface, 32 flange, 60 droplet detecting section, 61 camera, 100 infusion tube, 100a flange, 124 nozzle

The invention claimed is:
1. A fluid control device comprising:
a tubular infusion tube comprising a nozzle from which fluid drips;
a casing configured to house the infusion tube; and
a droplet detector configured to detect an amount of droplets dripping from the nozzle in the infusion tube housed in the casing,
wherein the infusion tube comprises a first flange protruding outward,
wherein the casing comprises:
a second flange configured to engage with the first flange in a direction along a longitudinal direction of the infusion tube and fix the infusion tube,
a fixation surface configured to fix the infusion tube in a direction orthogonal to the longitudinal direction of the infusion tube, and
a flap pivotably supported on an upper surface of the casing and being in contact with an upper portion of the infusion tube housed in the casing,
wherein the flap and the second flange hold the first flange in the infusion tube therebetween,
wherein the upper surface of the casing comprises a first upper surface and a second upper surface, and the second upper surface is higher than the first upper surface,
wherein the flap is arranged on the first upper surface, and wherein an upper surface of the flap in a first position is flush with the second upper surface.

2. The fluid control device according to claim 1, wherein the flap is switchable between the first position for regulating upward movement of the infusion tube and a second position for permitting the upward movement of the infusion tube.

3. The fluid control device according to claim 2, wherein the droplet detector comprises a camera configured to capture an image of the droplets dripping from the nozzle.

4. The fluid control device according to claim 1, wherein the flap is supported by a support shaft extending along a rear end of the upper surface of the casing, is pivotable in a front and rear direction of the casing, and has a cutout in a front surface of the flap.

5. The fluid control device according to claim 4, wherein the droplet detector comprises a camera configured to capture an image of the droplets dripping from the nozzle.

6. The fluid control device according to claim 1, wherein the droplet detector comprises a camera configured to capture an image of the droplets dripping from the nozzle.

7. The fluid control device according to claim 6, further comprising a frame member arranged inside the casing, and the camera is attached to the frame member,
wherein the second flange and the fixation surface are arranged integrally with the frame member.

8. A fluid control device comprising:
a tubular infusion tube comprising a nozzle from which fluid drips;
a casing configured to house the infusion tube; and
a droplet detector configured to detect an amount of droplets dripping from the nozzle in the infusion tube housed in the casing; and
a frame member arranged inside the casing,
wherein the infusion tube comprises a first flange protruding outward,
wherein the casing comprises:
    a second flange configured to engage with the first flange in a direction along a longitudinal direction of the infusion tube and fix the infusion tube,
    a fixation surface configured to fix the infusion tube in a direction orthogonal to the longitudinal direction of the infusion tube,
    a flap pivotably supported on an upper surface of the casing and being in contact with an upper portion of the infusion tube housed in the casing,
wherein the flap and the second flange hold the first flange in the infusion tube therebetween,
wherein the droplet detector comprises a camera configured to capture an image of the droplets dripping from the nozzle,
wherein the camera is attached to the frame member, and
wherein the second flange and the fixation surface are arranged integrally with the frame member.

* * * * *